US008784432B2

(12) United States Patent
Gagnepain et al.

(10) Patent No.: US 8,784,432 B2
(45) Date of Patent: Jul. 22, 2014

(54) PNEUMATIC VITREOTOME

(75) Inventors: Cédric Gagnepain, Pringy (FR); Jean-Marc Andre, Saint Alban Leysse (FR)

(73) Assignee: Corneal Innovation, Metz Tessy (FR)

( * ) Notice: Subject to any disclaimer, the term of this patent is extended or adjusted under 35 U.S.C. 154(b) by 139 days.

(21) Appl. No.: 12/440,380

(22) PCT Filed: Sep. 7, 2007

(86) PCT No.: PCT/FR2007/051889
§ 371 (c)(1),
(2), (4) Date: May 14, 2009

(87) PCT Pub. No.: WO2008/029066
PCT Pub. Date: Mar. 13, 2008

(65) Prior Publication Data
US 2009/0281479 A1    Nov. 12, 2009

(30) Foreign Application Priority Data

Sep. 8, 2006    (FR) .................................... 06 53635

(51) Int. Cl.
*A61F 9/00*    (2006.01)
(52) U.S. Cl.
USPC .......................................... 606/107; 606/171
(58) Field of Classification Search
CPC .................. A61B 10/0275; A61B 17/32002; A61B 2217/005; A61B 10/0283; A61B 10/0266; A61B 2010/0208; A61B 17/320016; A61B 17/320758; A61B 2010/0225; A61B 17/320783; A61F 9/00745; A61F 9/00763; A61F 9/00736

USPC .................. 606/107, 168, 170, 171; 604/22; 600/564, 565, 566, 567, 568
See application file for complete search history.

(56) References Cited

U.S. PATENT DOCUMENTS

| | | | | |
|---|---|---|---|---|
| 4,449,550 A * | 5/1984 | Ranalli | ................... | 137/624.13 |
| 4,577,629 A | 3/1986 | Martinez | | |
| 4,696,298 A | 9/1987 | Higgins | | |
| 5,782,397 A * | 7/1998 | Koukline | ................... | 227/176.1 |
| 6,575,990 B1 | 6/2003 | Wang | | |

FOREIGN PATENT DOCUMENTS

WO    WO 01/15640 A1    3/2001

* cited by examiner

*Primary Examiner* — Jonathan W Miles
(74) *Attorney, Agent, or Firm* — Kenyon & Kenyon LLP

(57) ABSTRACT

A vitreotomy device comprises a body extended by a cannula. The cannula has a closed distal end; it includes a window in its side wall close to said distal end. It houses a needle driven with reciprocating motion and capable of periodically closing said window. The device further comprises suction means connected to the needle, and a double-acting cylinder provided with a moving piston for controlling the movement of said needle. In said device, the needle is driven with reciprocating motion in translation in said cannula; said piston of the double-acting cylinder is secured directly to said needle; as a result, its movements enable the needle to be moved into a first position in which said needle closes said window, and a second position in which the needle leaves said window open. The device makes it possible to control very accurately the lengths of time for which the end of the cannula is open and closed.

8 Claims, 2 Drawing Sheets

PNEUMATIC VITREOTOME

This is a 371 national phase application of PCT/FR2007/051889 filed 7 Sep. 2007, claiming priority to French Patent Application No. 0653635 filed 8 Sep. 2006, the contents of which are incorporated herein by reference.

FIELD OF THE INVENTION

The present invention relates to a vitreotome, and more particularly to a vitreotome that is controlled pneumatically.

A vitreotome is a surgical instrument that makes it possible to act on the vitreous humor or vitreous body of a patient's eye.

Accompanying FIG. 1 is a longitudinal section of an eye. In this figure, there can be seen more particularly the cornea 12, the lens 14, the vitreous body 16 disposed in the eyeball 18 behind the lens 14, and also the retina 20 connected to the optic nerve 22. The vitreous body 16 is a gelatinous transparent substance (rather like egg white), that fills the cavity of the eye behind the lens. The vitreous body is made up of 95% water and its function is to give the eye its shape and its consistency. It thus represents 98% of the volume of the eye. Its role is to guarantee stiffness of the eyeball and in particular to hold the retina 20 in place against the wall 18 of the eye.

In simplified manner, a vitreotome comprises a cannula that can be inserted into the eye and that is fitted with a suction system and with a moving element that is mounted in the cannula to operate cyclically to cut away small quantities of the vitreous body that have been sucked into the cannula.

BACKGROUND OF THE INVENTION

U.S. Pat. No. 5,176,628 describes a pneumatically-controlled vitreotome. In that vitreotome, the sharp member is mounted to rotate inside the cannula. The reciprocating rotation of the sharp element is obtained by causing a piston to perform reciprocating motion under the control of pneumatic means. The piston has a rack that itself co-operates with a pinion that is secured to the rotary sharp tool.

Such a vitreotome suffers from the essential drawback of presenting an assembly for controlling movement of the sharp tool that is relatively complex and that includes a mechanical portion that makes obtaining accuracy over the movement of the sharp tool relatively random and that introduces a large amount of inertia in the control of the movement of the sharp tool of the vitreotome.

When performing a posterior vitreotomy, i.e. when intervening close to the retina, the vitreotome needs to ensure high-speed cutting with the length of time that the cannula is fully closed being as short and as stable as possible, even if the cutting speed is very high. The purpose of this is to avoid creating excessive suction inside the cannula which would run the risk of harming the retina on the next occasion the cannula is opened because of the large amount of suction that exists in the cannula.

SUMMARY OF THE INVENTION

An object of the present invention is to provide a pneumatically-controlled vitreotome that enables the opening and closing times at the end of the cannula to be controlled very accurately.

According to the invention, to achieve this object, the vitreotomy device comprises:
a body;
a cannula extending from one end of the body, said cannula presenting a closed distal end and being provided with a window in its side wall close to said distal end;
a needle driven with reciprocating motion in said cannula to close said window periodically;
suction means connected to said needle; and
a double-acting actuator provided with a moving piston for controlling the movement of said needle;
said device being characterized in that:
said needle is driven with reciprocating motion in translation inside said cannula; and
said double-acting actuator piston is secured directly to said needle and extends substantially perpendicularly to the axis of said needle, said movements of the piston being suitable for bringing said needle into a first position in which said needle closes said window, and a second position in which the distal end of the needle is spaced apart from the distal end of the cannula so as to leave said window open.

The term "directly secured" is used to mean that the connection between the piston of the actuator and the needle is provided rigidly without any intermediate part being interposed that can move relative to the piston or to the needle.

It will be understood that because the needle having its end constituting the sharp portion is connected directly to the piston of the actuator, and because the actuator is double-acting, it is possible to control the movements of the needle in translation inside the cannula with precision. It is thus possible to control accurately the lengths of time during which the window through which the vitreous body is sucked in is open and closed.

Preferably, said body forms two chambers of said actuator that are disposed on either side of said piston; and said piston comprises a plate secured to the proximal end of said needle and a deformable diaphragm of annular shape having one edge that is secured to the periphery of said plate and its other edge secured to said body.

Also preferably, the device further comprises a return spring interposed between said body and said piston, tending to return said needle towards its second position.

Also preferably, said body further comprises a first pipe for feeding the first chamber of the actuator and a second pipe for feeding the second chamber of the actuator.

Also preferably, the device includes connection means for connecting each pipe in alternation to a source of gas under pressure and to an exhaust, together with control means for controlling the connection means.

Also preferably, said control means control the connection means in such a manner that the complete travel cycle of the needle relative to the cannula is of constant duration and that, between two consecutive cycles, the distal end of the needle is maintained in its second position.

In the above-defined preferred embodiment, the needle is held between two cutting cycles in the position in which the window of the cannula remains open, thus avoiding creating any significant suction inside the cannula. Furthermore, the duration of the complete cutting cycle is a fixed duration and the cutting rate is determined by the time intervals between two cutting cycles.

BRIEF DESCRIPTION OF THE DRAWINGS

Other characteristics and advantages of the invention appear better on reading the following description of a preferred embodiment of the invention given as a non-limiting example. The description refers to the accompanying figures, in which.

DETAILED DESCRIPTION

Figure 1:
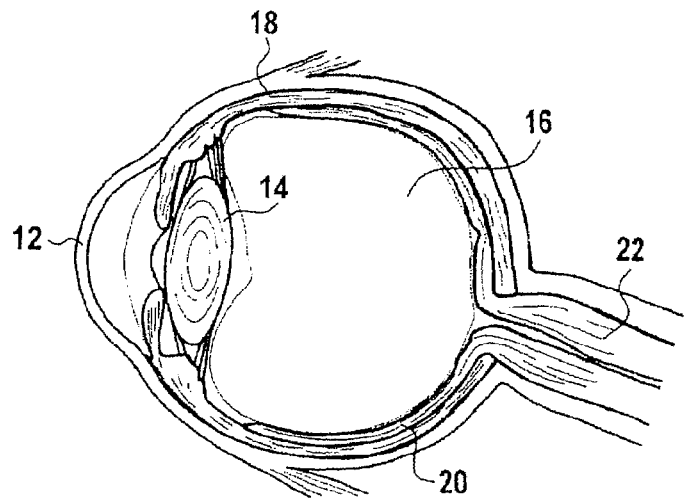
FIG. 1, described above, is a longitudinal section view of a human eye.
Figure 2A:
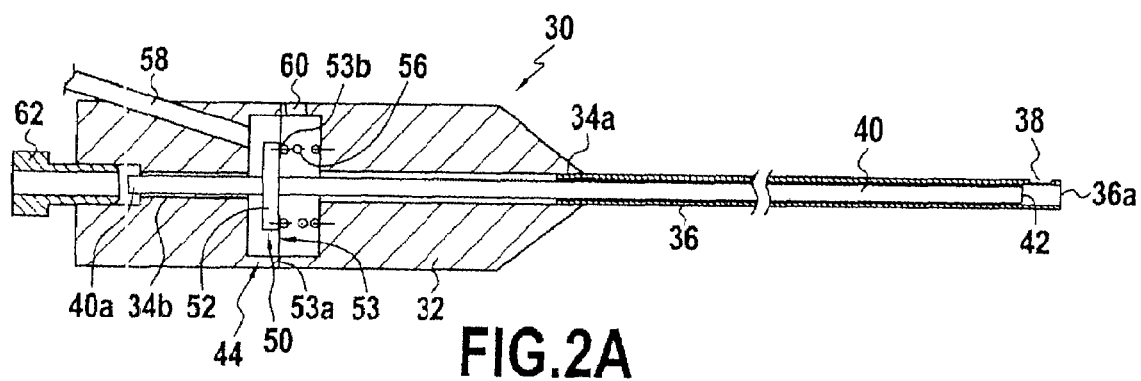
FIG. 2A is a longitudinal section of a vitreotome of the invention.
Figure 2B:
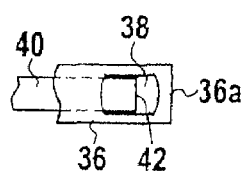
FIG. 2B is a fragmentary plan view of the end of the vitreotome cannula.

With reference initially to FIGS. 2A and 2B, there follows a description of the architecture of the vitreotome.

These figures show the vitreotome 30 in longitudinal section. The vitreotome comprises a preferably cylindrical body 32 having an axial passage 34 formed therein. A cylindrical cannula 36 is mounted at the distal end 34a of the passage. The distal end 36a of the cannula is closed, and a window 38 is formed in the side of the cannula close to the distal end 36a. A hollow needle 40 with a sharp distal end 42 is mounted to move in linear translation inside the axial passage 34 and the cannula 36. It can immediately be understood that by moving in translation inside the cannula 36, the needle 40 can disengage the window 42, or on the contrary can close it.

Movements of the needle 40 are controlled by a double-acting actuator 44. The actuator 44 is essentially constituted by two chambers 46 and 48 formed in the body 32 of the vitreotome. The chambers 46 and 48 are separated by a piston 50. The piston 50 is preferably constituted by a circular plate 52 secured to the needle 40, preferably close to its proximal end 40a, and by a diaphragm 53 of annular shape. The plate 52 is substantially perpendicular to the axis of the needle. The outer edge 53a of the diaphragm is secured to the body, while its inner edge 53b is secured to the periphery of the circular plate 52. In addition, a return spring 56 is interposed between the plate 52 and the wall of the chamber 48. The return spring tends to hold the needle 40 in its withdrawn position as shown in FIG. 2A, in which position the window 38 is open.

Two pipes 58 and 60 enable gas under pressure to be fed respectively to the chambers 46 and 48 of the double-acting actuator.

The proximal end 34b of the axial passage 34 is extended by a coupling endpiece 62 for connection to a suction hose. Thus, the suction effect is transmitted to the window when the needle is in its retracted position, thereby causing a small volume of the vitreous body to be inserted into the cannula. When the needle moves towards the distal end of the cannula, its sharp end cuts off the volume of the vitreous body that has been sucked in.

Figure 3:
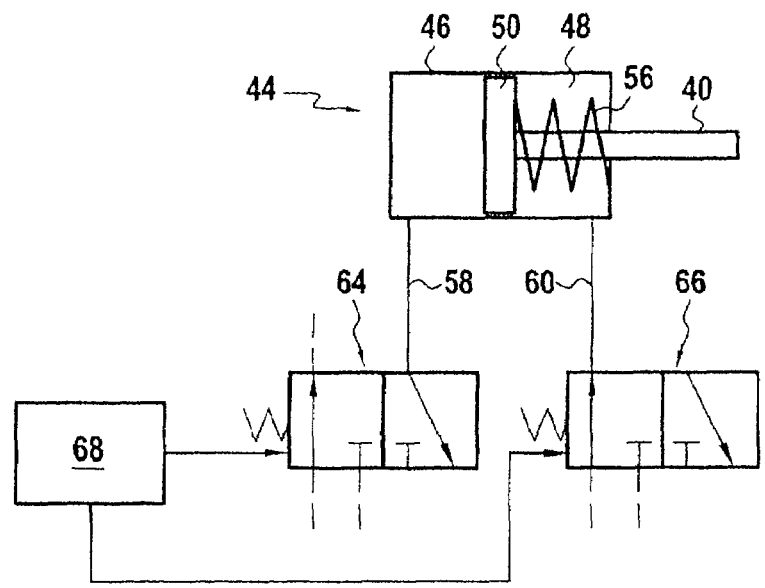
FIG. 3 is a diagram showing the compressed air feed to the actuator that controls movements of the needle.

FIG. 3 is a simplified diagram showing how the double-acting actuator 44 is controlled. Each of the feed pipes 58 and 60 is connected to a respective solenoid valve 64 or 66 suitable either for connecting the corresponding chamber to an exhaust, or for connecting it to a source of gas under pressure. The valves 64 and 66 are controlled by a control circuit 68.

Figure 4:
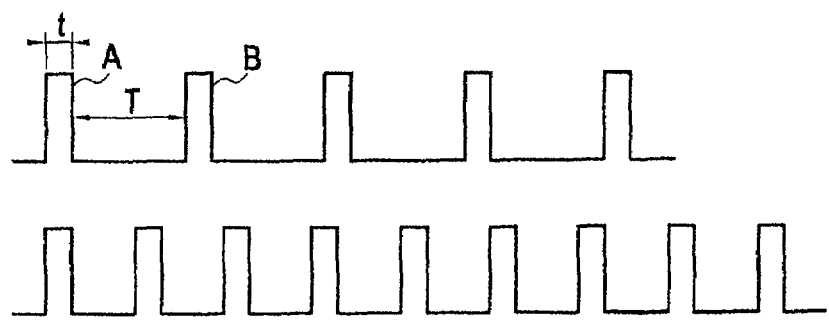
FIG. 4 shows two possible cycles for controlling movements of the needle inside the cannula.

FIG. 4 shows two possible operating cycles of the vitreotome. The pulses A, B, etc. shown in the two curves correspond to a complete opening and closing cycle of the window 38. During the cycle, the needle leaves its withdrawn position to cut off the piece of vitreous body that has been sucked in and then to close the window 38, and finally it returns to its initial position. As can be seen, the duration of this cycle is constant and equal to $t$. By way of example, $t$ is equal to 22 milliseconds (ms). In contrast, it is possible to adjust the duration of the period T between two consecutive operating cycles of the needle. During the time intervals T, the needle is held in its withdrawn position, in particular by the return spring 56.

The possibility of ensuring that the length of time the window is closed by the needle is very short makes it possible to optimize suction.

The invention claimed is:

1. A vitreotomy device comprising:
  a body;
  a cannula extending from one end of the body, said cannula presenting a closed distal end and being provided with a window in its side wall close to said distal end;
  a needle driven with reciprocating motion in said cannula to close said window periodically;
  a connecting member configured to connect a suction mechanism to said needle; and
  a double-acting cylinder provided with a movable piston for controlling the movement of said needle;
  a return spring interposed between said body and between said piston tending to return said needle towards a second position,
  wherein:
  said needle is driven with reciprocating motion in translation inside said cannula,
  said double-acting cylinder piston is secured directly to said needle and extends substantially perpendicularly to the axis of said needle, said movements of the piston being suitable for bringing said needle into a first position in which said needle closes said window, and a second position in which the distal end of the needle is spaced apart from the distal end of the cannula so as to leave said window open, and
  said piston comprises a plate secured to a proximal-half of said needle and a deformable diaphragm of annular shape having one edge that is secured to a front edge of said plate, the front edge being closer to the distal end of the cannula than its rear edge, and another edge of deformable diaphragm being secured to said body.

2. A device according to claim 1, wherein the distal end of said needle is sharp.

3. A device according to claim 1, wherein the proximal end of said needle is connected to the suction mechanism.

4. A device according to claim 1, wherein said body further comprises a first pipe for feeding a first chamber of said two chambers of the cylinder and a second pipe for feeding a second chamber of said two chambers of the cylinder.

5. A device according to claim 4, wherein the device includes a connection for connecting each pipe in alternation to a source of gas under pressure and to an exhaust, together with a control mechanism for controlling the connection.

6. A device according to claim 5, wherein said control mechanism controls the connection in such a manner that the complete travel cycle of the needle relative to the cannula is of constant duration and that, between two consecutive cycles, the distal end of the needle is maintained in its second position.

7. A device according to claim 4, wherein the first and second pipes are connected to respective solenoid valves, and the solenoid valves are controlled by a control circuit.

8. A vitreotomy device comprising:
  a body;
  a cannula extending at one end of the body, said cannula presenting a closed distal end and being provided with a window in its side wall close to said distal end;
  a needle driven with reciprocating motion in said cannula to close said window periodically;

a connecting member configured to connect a suction mechanism to said needle; and a double-acting cylinder provided with a movable piston for controlling the movement of said needle;

a return spring interposed between said body and between said piston tending to return said needle towards a second position, wherein said needle is driven with reciprocating motion in translation inside said cannula, wherein said double-acting cylinder position is secured directly to said needle and extends substantially perpendicularly to the axis of said needle, said movements of the piston being suitable for bringing said needle into a first position in which said needle closes said window, and the second position in which the distal end of the needle is spaced apart from the distal end of the cannula so as to leave said window open, wherein said body forms two chambers of said cylinder that are disposed on either side of said piston, wherein said piston comprises a plate secured to a proximal-half of said needle and a deformable diaphragm of annular shape having one edge that is secured to a front edge of said plate, the front edge being closer to the distal end of the cannula than its rear edge, and another edge of the deformable diaphragm being secured to said body, wherein the proximal end of said needle is connected to the suction mechanism, and wherein said body further comprises a first pipe for feeding a first chamber of said two chambers of the cylinder and a second pipe for feeding a second chamber of said two chambers of the cylinder.

* * * * *